(12) United States Patent
Noack

(10) Patent No.: US 9,649,019 B2
(45) Date of Patent: May 16, 2017

(54) METHOD AND DEVICE FOR RINSING ENDOSCOPE CHANNELS

(71) Applicant: OLYMPUS WINTER & IBE GMBH, Hamburg (DE)

(72) Inventor: Andreas Noack, Drage (DE)

(73) Assignee: Olympus Winter & IBE GMBH, Hamburg (DE)

( * ) Notice: Subject to any disclaimer, the term of this patent is extended or adjusted under 35 U.S.C. 154(b) by 411 days.

(21) Appl. No.: 14/210,637

(22) Filed: Mar. 14, 2014

(65) Prior Publication Data

US 2014/0190520 A1    Jul. 10, 2014

Related U.S. Application Data

(63) Continuation of application No. PCT/EP2012/003834, filed on Sep. 13, 2012.

(30) Foreign Application Priority Data

Sep. 15, 2011   (DE) .................... 10 2011 082 776

(51) Int. Cl.
    *A61B 1/12*     (2006.01)
    *A61B 90/70*     (2016.01)

(52) U.S. Cl.
    CPC .............. *A61B 1/125* (2013.01); *A61B 90/70* (2016.02); *A61B 2090/701* (2016.02)

(58) Field of Classification Search
    CPC .......................... A61B 1/125; A61B 2090/701
See application file for complete search history.

(56) References Cited

U.S. PATENT DOCUMENTS

| | | | |
|---|---|---|---|
| 5,738,824 A | 4/1998 | Pfeifer | |
| 2005/0065405 A1 | 3/2005 | Hasegawa | |
| 2009/0060798 A1 | 3/2009 | Williams et al. | |

FOREIGN PATENT DOCUMENTS

| | | |
|---|---|---|
| DE | 10321991 B3 | 5/2004 |
| DE | 102004040734 B3 | 9/2005 |
| EP | 0711529 A1 | 5/1996 |
| WO | 2004/049925 A1 | 6/2004 |

OTHER PUBLICATIONS

International Search Report dated Nov. 23, 2012 issued in PCT/EP2012/003834.

*Primary Examiner* — Jason Ko
(74) *Attorney, Agent, or Firm* — Scully, Scott, Murphy & Presser, P.C.

(57) ABSTRACT

A method for rinsing endoscope channels of an endoscope with a rinsing agent from a rinsing agent supply. The method including: connecting a first endoscope channel to the rinsing agent supply via a first rinsing agent distributor, which has a testing device for checking an endoscope channel for a blockage; connecting at least one other endoscope channel to the rinsing agent supply via a second rinsing agent distributor; and checking the first endoscope channel for a blockage using a testing device and simultaneously rinsing the at least one other endoscope channel with rinsing agent from the rinsing agent supply. A device is also provided for rinsing endoscope channels of an endoscope with rinsing agent from a rinsing supply.

9 Claims, 2 Drawing Sheets

METHOD AND DEVICE FOR RINSING ENDOSCOPE CHANNELS

CROSS-REFERENCE TO RELATED APPLICATION

This application is a continuation application of PCT/EP2012/003834 filed on Sep. 13, 2012 and claims benefit of Application No. DE 10 2011 082 776.5 filed on Sep. 15, 2011, the entire contents of each of which are incorporated herein by this reference.

BACKGROUND

Field

The invention relates to a method for rinsing endoscope channels of an endoscope. The invention further relates to a device for the rinsing of endoscope channels of an endoscope and the use of a corresponding device.

Prior Art

During the preparation of endoscopes with one or more channels, they are normally rinsed and simultaneously checked for blockages. For this, a measuring device, for example a flow meter or a pressure meter, are provided in the rinse line.

In the case of endoscopes with several channels, the channels are either rinsed and checked individually one after the other or simultaneously.

The effort for a rinsing of the channels one after the other is relatively low, since only one measuring device is needed. However, the entire processing time or cleaning time is relatively long, since the rinsing times to be maintained for each channel add up.

The processing time is reduced considerably when the channels are rinsed in parallel. However, the effort for the flow check increases with the number of channels because a measuring device with associated electronics must be provided for each channel.

SUMMARY

The object of the invention is to keep the processing time for the cleaning of an endoscope with several endoscope channels as short as possible and to minimize the required effort.

This object is solved through a method for rinsing endoscope channels of an endoscope with rinsing agent from a rinsing agent supply comprising the following method steps:

connecting a first endoscope channel to the rinsing agent supply via a first rinsing agent distributor, which has a testing device for checking an endoscope channel for a blockage;

connecting at least one other endoscope channel to the rinsing agent supply via a second rinsing agent distributor;

checking the first endoscope channel for a blockage by means of the testing device and simultaneously rinsing the at least one other endoscope channel with rinsing agent from the rinsing agent supply.

According to the invention, the endoscope channels of an endoscope are thus checked one after the other for blockages, but in parallel or simultaneously additional endoscope channels or respectively at least one additional endoscope channel are rinsed. Since the duration for checking an endoscope channel for a blockage is generally considerably shorter than the provided or prescribed time for the rinsing and cleaning of the endoscope channel, a considerable portion of the processing time is saved through the parallel rinsing. At the same time, the effort remains low regardless of the number of endoscope channels, because a single testing device is sufficient according to the invention. Preferably, several other or all other endoscope channels are rinsed simultaneously.

When the aforementioned method steps are repeated, wherein, in particular respectively, one other endoscope channel is connected to the rinsing agent supply as the first endoscope channel via the first rinsing agent distributor, it is ensured in particular that a secure checking for blockages takes place for all endoscope channels and the proper rinsing duration can simultaneously be met for all endoscope channels.

It is preferably provided that a flow rate or a pressure of the rinsing agent is measured or determined for checking an endoscope channel for a blockage by means of the testing device. Pressure and flow rate are in particular dependent on the diameter of an endoscope channel, which changes, in particular decreases, in the case of a partial or complete blockage. The measuring or determining of the pressure and/or flow rate, in particular of a volume flowing per time unit, thus ensures that a blockage of an endoscope or respectively of an endoscope channel is securely detected.

Advantageously, the method according to the invention is terminated as soon as the checking for an endoscope channel shows a blockage. In this case, it is generally prescribed that the endoscope must be specially handled or discharged so that a continuation of the method according to the invention would only unnecessarily extend the processing time.

The object is also solved through a device for rinsing endoscope channels of an endoscope with rinsing agent from a rinsing agent supply, wherein the device comprises a first rinsing agent distributor and a second rinsing agent distributor, each of which are connected to the rinsing agent supply, as well as a number of rinsing channels for feeding rinsing agent from the rinsing agent supply into respectively one endoscope channel, wherein a switching valve is provided for each rinsing channel, by means of which the rinsing channel is connected in a first position of the switching valve with the first rinsing agent distributor and in a second position with the second rinsing agent distributor, wherein the first rinsing agent distributor comprises a first testing device, by means of which an endoscope channel connected to the first rinsing agent distributor via one of the rinsing channels can be checked for a blockage.

A rinsing agent is in particular a rinsing liquid, for example a disinfecting solution.

A rinsing channel is in particular a connection for an endoscope channel or comprises a connection for an endoscope channel.

The number of rinsing channels is preferably greater than or equal to a number of endoscope channels of an endoscope to be rinsed so that each endoscope channel can be connected to exactly one rinsing channel. After the connection of the endoscope to the device or respectively the endoscope channels to the rinsing channels, a cleaning of all endoscope channels together is thereby enabled. In particular, the cleaning process, which runs for example automatically, can be performed for all endoscope channels of an endoscope without interruption.

The second rinsing agent distributor preferably has a second testing device. In particular, the possibility of a redundant check of an endoscope channel for a blockage, namely by means of the first testing device on one hand and by means of the second testing device on the other hand, is hereby given.

The first testing device and/or the second testing device preferably comprise a flow meter or a pressure meter. In particular, one of the two testing devices can comprise a flow meter and the other of the two testing devices, a pressure meter. In the design as flow meter, the second testing device can preferably measure the overall flow through the other channels.

A flow meter determines in particular the quantity, in particular the volume, of rinsing agent flowing per time unit through a testing device or respectively the associated rinsing agent distributor. A blockage in an endoscope channel, which is connected in particular as single endoscope channel to the corresponding rinsing agent distributor or is connected with it, is recognizable in particular in that the measured or determined flow rate of the rinsing agent deviates from the flow rate expected for this endoscope channel. With this measurement principle, in particular partial blockages or constrictions in an endoscope channel are also detectable, in the case of which the endoscope channel is not closed or blocked completely.

By means of a pressure meter, in particular the pressure of the rinsing agent is measured or determined in the testing device or respectively the corresponding rinsing agent distributor, which is directly linked with the rinsing agent pressure within an endoscope channel connected to the rinsing agent distributor. Blockages or constrictions of the endoscope channel are also hereby detectable, because the cross-section of the endoscope channel, which is reduced by deposits or blockages, has a direct impact on the rinsing agent pressure in the endoscope channel.

It is particularly preferred if a rinsing agent distributor is designed as a rinsing agent chamber or as a rinsing agent reservoir. A particularly compact rinsing agent distributor with very short line paths is thereby enabled, which are preferred over longer and/or branched lines for hygienic reasons.

It is also particularly preferred if a switching valve has an in particular automatically controllable actuating drive. The rinsing, cleaning and checking of the endoscope channels after an, in particular specified, cleaning procedure can take place automatically, i.e. in particular without intervention from an operator.

If a rinsing channel in a third position of the corresponding switching valve is not connected with any of the rinsing agent distributors, a rinsing channel or respectively endoscope channel, which was already rinsed for a sufficiently long period of time, can be completely separated from the rinsing agent supply so that the efficiency of the rinsing device is increased because in particular rinsing agent is saved. Moreover, rinsing channels, to which no endoscope channel is connected, can be closed during the cleaning. A larger number of rinsing channels can thus be provided, which is possible without great effort due to the invention, so that a single device according to the invention for rinsing or cleaning different endoscopes or endoscope types with different numbers of endoscope channels or also for the cleaning of several endoscopes simultaneously can be used.

It is preferably provided that the device comprises a rinsing agent pump in order to supply at least one rinsing agent distributor with rinsing agent from the rinsing agent supply under an, in particular specifiable, pressure. In particular the precision of the test and the controllability of the cleaning process, in particular of the rinsing, are hereby increased.

It is also advantageous if the device comprises at least one, in particular connectible, pressure booster pump, for example in a supply line from the rinsing agent supply to the first rinsing agent distributor. The pressure booster pump can also be arranged in one of the rinsing channels. The pressure of the rinsing agent in the endoscope channels or in a part of the endoscope channels can hereby be specified separately. This is in particular advantageous for the testing of individual, relatively narrow endoscope channels, for example of an Albarran channel.

The device according to the invention is characterized in particular in that it is suitable for the use of the method according to the invention.

The object of the invention is also solved through the use of a device according to the invention in a method according to the invention.

During the rinsing of the endoscope, a rinsing agent that is a cleaning solution is normally used. For example, a disinfecting solution can be used for example or a solution, which acts in an antibacterial manner. Rinsing agent solutions for this are known to a person skilled in the art. After the respective endoscope has been sufficiently cleaned, it is rinsed with clean water in order to eliminate any chemical components of the rinsing agent solutions or respectively of the rinsing agent. In particular, the switching valves are hereby switched such that all rinsing agent residues are rinsed out.

Further characteristics of the invention will become apparent from the description of the embodiments according to the invention together with the claims and the included drawings. Embodiments according to the invention can fulfil individual characteristics or a combination of several characteristics.

BRIEF DESCRIPTION OF THE DRAWINGS

The invention is described below, without restricting the general idea of the invention, using exemplary embodiments with reference to the drawings, wherein we expressly refer to the drawings with regard to the disclosure of all details according to the invention that are not explained in greater detail in the text. They show in.

DETAILED DESCRIPTION

Figure 1:
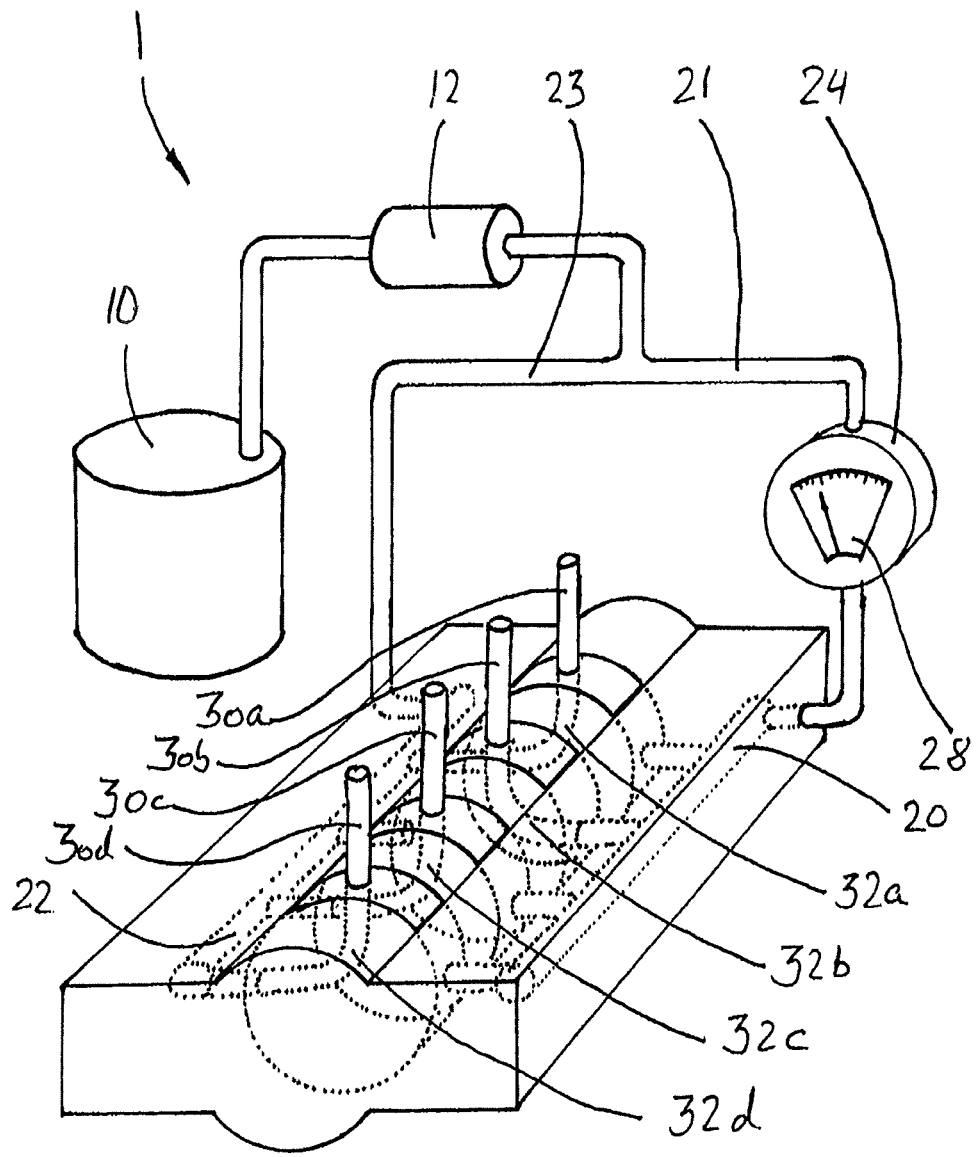
FIG. 1 schematically illustrates a rinsing device according to the invention and FIG. 2 schematically illustrates a circuit diagram of another rinsing device according to the invention.

In the drawings, the same or similar types of elements and/or parts are provided with the same reference numbers in order to prevent the item from needing to be reintroduced.

FIG. 1 shows schematically a rinsing device 1 according to the invention with four rinsing channels 30a, 30b, 30c, 30d. An endoscope (not shown) is connected to the rinsing device, wherein respectively one endoscope channel is connected with a rinsing channel. The cleaning of the endoscope or respectively of the endoscope channels takes place with rinsing agent, which is introduced into the endoscope channels via the rinsing channels.

The rinsing agent, for example a liquid disinfecting solution, is provided in a rinsing agent reservoir 10 and conveyed by means of a pump 12 over a first supply line 21 into a first distribution chamber 20 as well as via a second supply line 23 into a second distribution chamber 22.

Moreover, a testing device 24 with a flow meter 28 is provided in the first supply line 21 to the first distribution chamber 20. The flow meter 28 is in particular a flow volume meter, i.e. the rinsing agent volume flowing per time unit through the first supply line 21 is measured or determined.

Alternatively, a flow meter 28 can also be a flow mass meter, i.e. the mass of the rinsing agent flowing per time unit through the first supply line is measured or determined. The size to be determined can thereby correspond respectively with the measured measurement value or can be determined from the measurement value.

Switching valves 32*a-d* are arranged between the rinsing channels 30*a-d* on one side and the two distribution chambers 20, 22 on the other side, wherein a separate switching valve 32*a-d* is provided for each rinsing channel 30*a-d*. This thus results in a reciprocal assignment of respectively one switching valve 32*a-d*, one rinsing channel 30*a-d* and one endoscope channel connected to this rinsing channel 30*a-d*.

A switching valve 32*a-d* is respectively designed such that the corresponding rinsing channel 30*a-d* in a first position of the switching valve 32*a-d* is connected with the first distribution chamber 20 and in a second position of the switching valve 32*a-d* with the second distribution chamber 22. The corresponding endoscope channel is thus fed or supplied with rinsing agent via the first distribution chamber 20 or the second distribution chamber 22.

The switching valves 32*a-d* are for example turned for switching between the first position and the second position. For this, the switching valves 32*a-d* respectively have an actuating drive (not shown), for example an adjusting cylinder or a worm drive.

In the first position (position A) of the switching valve 32*a*, the rinsing agent thus flows from the rinsing agent supply 10, supported by the pump 12, via the first supply line 21 and the testing device 24, the first distribution chamber 20, the switching valve 32*a* and the rinsing channel 30*a* to a endoscope channel connected to the rinsing channel 30*a*. If the switching valve 32*a* is switched, i.e. brought into the second position (position B), the endoscope channel is in contrast supplied with rinsing agent and rinsed via the second supply line 23, the second distribution chamber 22, the switching valve 32*a* and the rinsing channel 30*a*. The same goes for the switching valve 32*b* and an endoscope channel connected to the rinsing channel 30*b*, the switching valve 30*c* and an endoscope channel connected to the rinsing channel 30*c* as well as the switching valve 32*d* and an endoscope channel connected to the rinsing channel 30*d*.

FIG. 1 shows an example of a state of the rinsing device 1, in which the rinsing valve 32*b* is located in position A and the other switching valves 32*a*, 32*c*, 32*d* are in position B. An endoscope channel connected to the rinsing channel 30*b* is thus supplied with rinsing agent via the first supply line 21 and the first distribution chamber 20, while the rinsing agent arrives at endoscope channels connected to the other rinsing agent channels 30*a*, 30*c*, 30*d* via the second supply line 23 and the second distribution chamber 22.

Since only the rinsing channel 30*b* is connected with the first supply line 21, the rinsing agent volume measured or determined by means of the flow meter 28 corresponds with the rinsing agent quantity that flows through the endoscope channel connected to the rinsing channel 30*b*. If this endoscope channel is completely or partially blocked, the rinsing agent volume flowing per time unit through the endoscope channel changes, which is measurable by the flow meter 28. The endoscope channel 30*b* can thus be checked for a blockage by means of the flow meter 28 or respectively the testing device 24.

Accordingly, the endoscope channels connected to the other rinsing channels 30*a*, 30*c*, 30*d* can be checked respectively for a blockage when the switching valves 32*a-d* are changed or switched such that respectively the switching valve 32*a-d* assigned to the corresponding endoscope channel is brought or will be brought into position A and all other switching valves 32*a-d* into position B.

All other endoscope channels are supplied with rinsing agent and cleaned or rinsed via the second supply line 23 as well as the second distribution chamber 22.

For the cleaning of an endoscope, all endoscope channels are connected individually and one after the other to the first distribution chamber 20 and checked for blockages in the described manner by means of the, testing device 24 through corresponding adjustment of the switching valves 32*a-d*. The respective other endoscope channels are simultaneously connected with the second distribution chamber 22 and rinsed.

For example, the position combinations for the switching valves 32*a-d* shown in the following table are thereby set one after the other for an exemplary endoscope with four endoscope channels:

| No. | 32a | 32b | 32c | 32d |
| --- | --- | --- | --- | --- |
| 1 | A | B | B | B |
| 2 | B | A | B | B |
| 3 | B | B | A | B |
| 4 | B | B | B | A |
| 5 | B | B | B | B |

In the table, a row shows a combination of the simultaneously set positions of all switching valves 32*a-d* and a column shows the successive positions for a specific switching valve 32*a*, 32*b*, 32*c*, 32*d*. In this example, position A means that the corresponding endoscope channel is checked for a blockage, while position B means that the corresponding endoscope channel is rinsed.

In the case of the first combination, provided with the sequential number 1, the switching valve 32*a* is located in position A, i.e. an endoscope channel connected to the rinsing channel 30*a* is checked for a blockage by means of the testing device 24. The other switching valves 32*b*, 32*c*, 32*d* are located in position B so that the corresponding endoscope channels are rinsed simultaneously. This configuration is retained until a test for blockage or a passage test of the endoscope channel connected to the rinsing channel 30*a* is performed with the desired accuracy. The duration of the corresponding test can vary in particular depending on the cross-section of the endoscope channel to be checked.

The switching valves 32*a-d* are subsequently brought into the configuration designated with the sequential number 2, in which the switching valve 32*b* is in position A and the other switching valves 32*a*, 32*c*, 32*d* are in position B. The endoscope channel connected to the rinsing channel 30*b* is now checked for a blockage and the endoscope channels connected to the other rinsing channels 32*a*, 32*c*, 32*d* are rinsed.

In this manner, all four endoscope channels are checked for a blockage one after the other, wherein the respective duration for the performance of the test and correspondingly the duration, for which one of the combinations of valve positions is retained, can differ from endoscope channel to endoscope channel or respectively from combination to combination. The duration of the individual tests is thereby selected in particular such that a test takes place for all endoscope channels with comparable precision.

The total duration for running through configurations 1 to 4 thus results from the addition of the times required for the testing of the individual endoscope channels or respectively the testing times for the individual endoscope channels. A certain rinsing duration, which mainly corresponds with the addition of the testing times used for all other endoscope channels, thereby results automatically for each endoscope channel and without additional time loss. It should thereby be taken into consideration if applicable that an endoscope channel is rinsed with rinsing agent depending on the functionality of the testing device 24 if applicable also during the testing for a blockage, which can then be taken into consideration for the already carried out rinsing duration of this endoscope channel.

If the rinsing duration achieved by running through configurations 1 to 4 for one or more endoscope channels is not yet sufficient for a proper cleaning of the endoscope channel(s), then a configuration 5 can be set if applicable, in which for example all switching valves 32a-d are in position B and thus all endoscope channels are rinsed one more time for a potentially required remaining duration.

Figure 2:
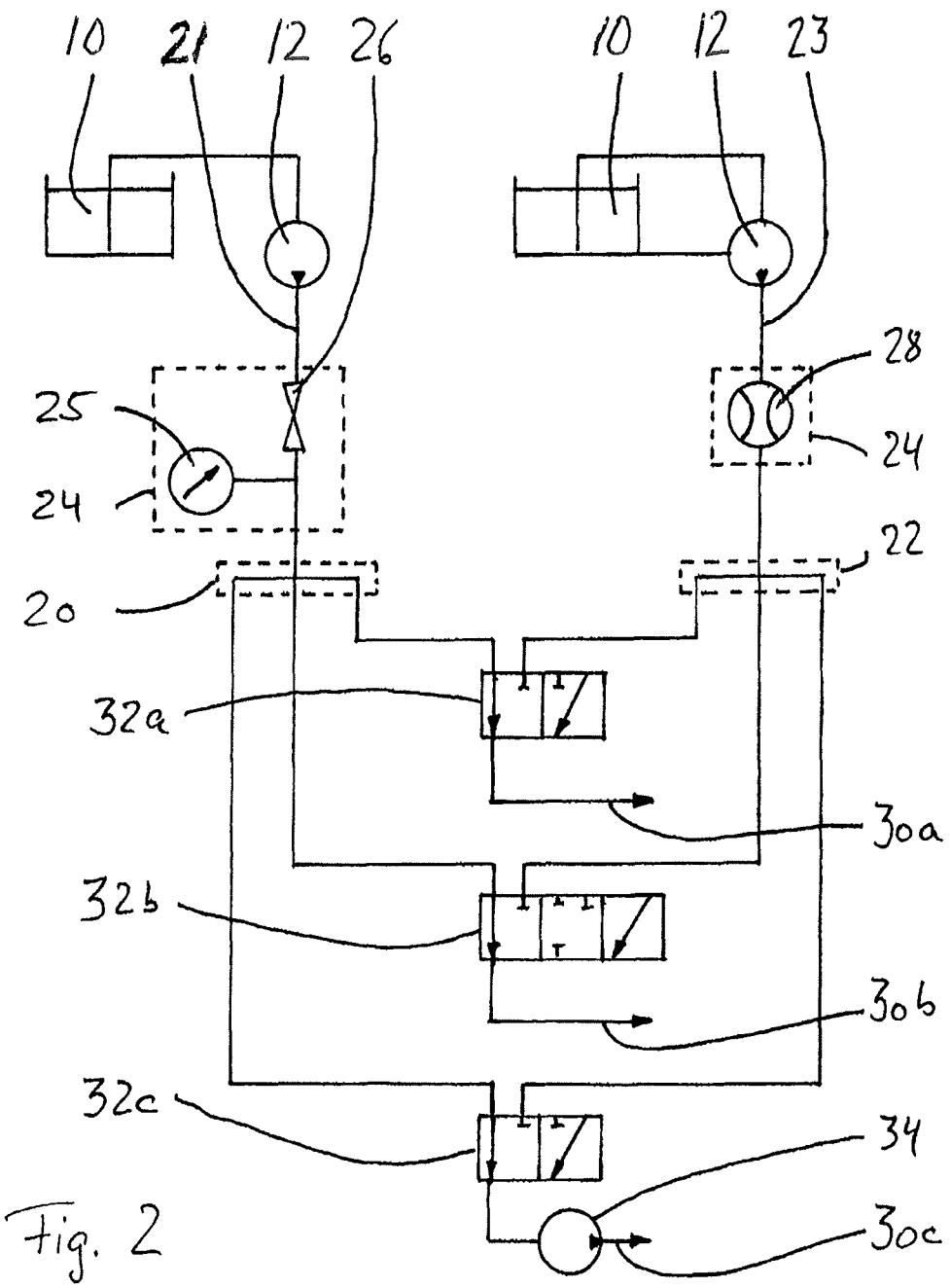

FIG. 2 shows schematically a circuit diagram of another rinsing device 1 according to the invention, from which examples of a few further embodiments and variations of the invention can be seen.

The rinsing device shown in FIG. 2 has as examples three rinsing channels 30a, 30b, 30c, each of which are connectible with a first distributor 20 or a second distributor 22 via a distribution valve 32a, 32b, 32c. The distributors 20, 22 each have a supply line 21, 23 for supplying rinsing agent, which can be distributed to endoscope channels of a connected endoscope via the switching valves 32a-c and rinsing channels 30a-c.

Both supply lines 21, 23 are each equipped separately with a rinsing agent supply 10 and a pump 12. Each of the distributors 20, 22 can thereby be supplied for example with a different rinsing agent and/or supplied with rinsing agent under a different pressure.

A testing device 24 is provided with a cutoff valve 26 and a pressure meter 25 in the supply line 21. A blockage downstream of this testing device 24 is detectable in that the pressure in the supply line 21 measured by means of the pressure meter 25, which is arranged downstream of the cutoff valve 26, does not fall or only falls slowly after the cutoff valve 26 is closed. Mainly a change or respectively constriction of the cross-section of an endoscope channel is also hereby demonstrated.

The supply line 23 also has a testing device 24, wherein this testing device comprises a flow meter 28 with the functionality already described in connection with FIG. 1.

The described testing devices are to be understood as examples within the framework of the invention. In particular, the scope of protection of the invention includes any testing device, with which an endoscope channel connected downstream is testable for a blockage or respectively by means of which a blockage of the endoscope channel can be detected or demonstrated.

The switching valve 32a of the exemplary rinsing device 1 shown in FIG. 2 is designed as 3/2-way valve, wherein in the first position rinsing agent is directed out of the distributor 20 and in the second position rinsing agent is directed out of the distributor 22 to a rinsing channel 30a, to which in turn an endoscope channel is or will be connected. The functionality of the switching valve 32a thus mainly corresponds with the switching function described in connection with FIG. 1.

The switching valve 32b is designed as a 3/3-way valve. In a first position, rinsing agent is directed out of the distributor 20 into the rinsing channel 30b. In a second position, rinsing agent is directed out of the distributor 22 into the rinsing channel 30b. In a third position, the valve is closed, i.e. no rinsing agent is flowing. The rinsing channel 30b is thus a rinsing channel that can be switched off, which can remain free for example if the endoscope to be rinsed has fewer endoscope channels than there are rinsing channels 30a-c. This functionality is particularly advantageous in the case of a rinsing device with numerous, for example more than five, rinsing channels.

The switching valve 32c in FIG. 2 is designed in turn as a 3/2-way valve, comparable with the switching valve 32a. It can however be designed as a 3/3-way valve or in another suitable manner without giving up the main idea according to the invention.

The rinsing channel 30c connected to the switching valve 32c has an auxiliary pump 34, by means of which the rinsing agent pressure in the rinsing channel 30c and the connected endoscope channel is specifiable regardless of the rinsing agent pressure in the other rinsing channels or endoscope channels. The rinsing channel 30c is particularly suitable for particularly narrow endoscope channels, for example an Albarran channel, which are advantageously rinsed under a relatively high pressure, in order for example to reduce the required rinse duration.

Due to the fact that one rinsing device 24 is provided in both the supply line 21 and the supply line 23, an endoscope channel can be checked for a blockage in two independent manners. In particular, a redundant test can take place. It can hereby be excluded for example that an endoscope channel, which is actually open, is incorrectly displayed as being blocked due to a switching valve 32a-d blocked on one side, a problem with a distributor 20, 22 or a faulty supply line 21, 23.

An exemplary endoscope has three endoscope channels with different diameters. For the cleaning by means of the rinsing device shown in FIG. 2, for example the thinnest endoscope channel, i.e. the endoscope channel with the smallest cross-section or the greatest flow resistance, is connected to the rinsing channel 32c, which has the auxiliary pump 34. The thickest endoscope channel or respectively the endoscope channel with the lowest flow resistance is connected for example to the blockable rinsing channel 32b and the third endoscope channel to the rinsing channel 32a.

The cleaning of the endoscope or respectively the rinsing and testing of the endoscope channels takes place for example with the following combinations of positions set one after the other for the switching valves 32a-c:

| No. | 32a | 32b | 32c |
|---|---|---|---|
| 1 | A | B | B |
| 2 | B | A | B |
| 3 | B | B | A |
| 4 | B | A | A |
| 5 | A | B | A |
| 6 | A | C | B |

Position A thereby means that the corresponding endoscope channel is connected with the first distributor 20; position B means that the endoscope channel is connected with the second distributor 22 and position C, which is only provided for the switching valve 32b, that the corresponding endoscope channel is altogether separated from both distributors 20, 22 and thus from the rinsing agent supply.

In the combinations 1 to 3, one after the other, each of the endoscope channels alone is connected with the first distributor 20 and is checked for a blockage by means of the first testing device 24 in the supply line 21, i.e. by means of the cutoff valve 26 and pressure meter 25. The other two endoscope channels are simultaneously supplied with rinsing agent and rinsed via the second distributor 22.

In the combinations 4 to 6, one after the other, each of the endoscope channels alone is connected with the second distributor 22 and is checked for a blockage by means of the second testing device 24 in the supply line 23, i.e. by means of the flow meter 28.

In the combination 6, the switching valve 32*b* is located in position C, in which the corresponding endoscope channel is separated from the rinsing agent supply. This is for example the endoscope channel with the lowest flow resistance, which generally requires the shortest rinsing duration for proper cleaning. Rinsing agent is saved in this manner.

When running through combinations 1 to 6, each endoscope channel is checked for a blockage two times, wherein respectively different testing methods or measuring methods are used. Thus, there are two independent and redundant tests for each endoscope channel so that in particular mechanical errors, for example a switching valve 32*a-c* blocked on one side or a faulty distributor 20, 22, can be detected and fixed.

Moreover, different testing processes can deliver different exact results or respectively can require different lengths for a certain precision of the test depending for example on the cross-section of an endoscope channel. If two different testing devices 24 are provided, as in the example shown in FIG. 2, an additional time savings is realized in that each endoscope channel is tested by means of the testing device 24, by means of which an identically exact or better test result is to be achieved in a short period of time. In particular for endoscopes, which have endoscope channels with different diameters due to the design, further shortening of the processing time for the cleaning is possible here.

All named characteristics, including those taken from the drawings alone, and individual characteristics, which are disclosed in combination with other characteristics, are considered alone and in combination as important to the invention. Embodiments according to the invention can be fulfilled through individual characteristics or a combination of several characteristics.

List of References

1 Rinsing device
10 Rinsing agent supply
12 Pump
20 Rinsing agent distributor
21 Supply line
22 Rinsing agent distributor
23 Supply line
24 Testing device
25 Pressure meter
26 Cutoff valve
28 Flow meter
30 Rinsing channel
32 Switching valve
34 Auxiliary pump

What is claimed is:

1. A device for rinsing endoscope channels of an endoscope with rinsing agent from a rinsing agent supply, wherein the device comprises:
   a first rinsing agent distributor and a second rinsing agent distributor, each of the first and second rinsing agent distributors being connected to the rinsing agent supply;
   rinsing channels connected to the first and second rinsing agent distributors for feeding rinsing agent from the rinsing agent supply into a respective endoscope channel,
   a switching valve provided for each of the rinsing channels for connecting each of the rinsing channels in a first position of the switching valve with the first rinsing agent distributor and in a second position of the switching valve with the second rinsing agent distributor, and
   a first testing device connected with the first rinsing agent distributor for checking whether an endoscope channel connected to the first rinsing agent distributor via one of the rinsing channels is blocked.

2. The device according to claim 1, further comprising a second testing device connected with the second rinsing agent distributor.

3. The device according to claim 1, wherein the first testing device comprises one of a flow meter or a pressure meter.

4. The device according to claim 2, wherein the second testing device comprises one of a flow meter or a pressure meter.

5. The device according to claim 1, wherein one or more of the first and second rinsing agent distributors is configured as a rinsing agent chamber or as a rinsing agent reservoir.

6. The device according to claim 1, wherein the switching valves include an automatically controllable actuating drive.

7. The device according to claim 1, wherein one or more of the switching valves includes a third position where a corresponding one of the rinsing channels is not connected to the first or second rinsing agent distributors.

8. The device according to claim 1, further comprising a rinsing agent pump to supply at least one of the first and second rinsing agent distributors with rinsing agent from the rinsing agent supply under a specifiable pressure.

9. The device according to claim 1, further comprising at least one pressure booster pump provided in a supply line from the rinsing agent supply to the first rinsing agent distributor.

* * * * *